United States Patent
Lima et al.

(10) Patent No.: US 10,982,739 B2
(45) Date of Patent: Apr. 20, 2021

(54) BI-STABLE ACTUATOR DEVICES

(71) Applicant: Lintec of America, Inc., Richardson, TX (US)

(72) Inventors: Marcio Dias Lima, Richardson, TX (US); Luis Plata, Richardson, TX (US); Yang Yang, Richardson, TX (US)

(73) Assignee: LINTEC OF AMERICA, INC., Richardson, TX (US)

( * ) Notice: Subject to any disclaimer, the term of this patent is extended or adjusted under 35 U.S.C. 154(b) by 153 days.

(21) Appl. No.: 16/097,555

(22) PCT Filed: Apr. 28, 2017

(86) PCT No.: PCT/US2017/030199
§ 371 (c)(1),
(2) Date: Oct. 29, 2018

(87) PCT Pub. No.: WO2017/190054
PCT Pub. Date: Nov. 2, 2017

(65) Prior Publication Data
US 2019/0154122 A1    May 23, 2019

Related U.S. Application Data

(60) Provisional application No. 62/350,113, filed on Jun. 14, 2016, provisional application No. 62/329,803, filed on Apr. 29, 2016.

(51) Int. Cl.
*F16H 19/06* (2006.01)
*A61F 2/30* (2006.01)
(Continued)

(52) U.S. Cl.
CPC .......... *F16H 19/0654* (2013.01); *A61F 2/30* (2013.01); *F03G 7/06* (2013.01); *H02N 11/006* (2013.01); *D01F 6/00* (2013.01); *H02N 10/00* (2013.01)

(58) Field of Classification Search
CPC ..... A61F 2/30; D01F 6/00; F03G 7/06; F16H 19/0654; H02N 10/00; H02N 11/006; D01D 5/0007; D01B 2401/046
See application file for complete search history.

(56) References Cited

U.S. PATENT DOCUMENTS

| 4,843,921 A | 7/1989 | Kremer |
| 5,396,769 A * | 3/1995 | Brudnicki ............... F03G 7/065 60/527 |

(Continued)

FOREIGN PATENT DOCUMENTS

| CN | 103904933 A | 7/2014 |
| JP | H06126681 A | 5/1994 |

(Continued)

OTHER PUBLICATIONS

International Preliminary Report on Patentability issued in corresponding International Application No. PCT/US2017/030199 dated Oct. 30, 2018 (7 pages).

(Continued)

*Primary Examiner* — Jesse S Bogue
(74) *Attorney, Agent, or Firm* — Greenblum & Bernstein, P.L.C.

(57) ABSTRACT

An actuator device that includes a first actuating segment of an artificial muscle fiber, where one end of the first actuating segment is connected to a first terminal and the other end of the first actuating segment is connected to a second terminal. The device also includes a second actuating segment of an artificial muscle fiber, where one end of the second actuating segment is connected to a third terminal and the other end of the second actuating segment is connected to a fourth terminal. The device also includes a paddle disposed on both the first and second actuating segments and a heating provision disposed on the first and second actuating segments. The heating provision independently provides energy (Continued)

in the form of heat to the first and second actuating segments, and the actuator device moves rotates the paddle to a desired position through activating the first or second actuating segments.

21 Claims, 10 Drawing Sheets

(51) Int. Cl.
*F03G 7/06* (2006.01)
*H02N 11/00* (2006.01)
*D01F 6/00* (2006.01)
*H02N 10/00* (2006.01)

(56) References Cited

U.S. PATENT DOCUMENTS

| | | | |
|---|---|---|---|
| 5,685,149 A * | 11/1997 | Schneider | F03G 7/06 250/573 |
| 9,784,249 B2 | 10/2017 | Li et al. | |
| 2006/0261709 A1* | 11/2006 | Kato | F03G 7/06 310/367 |
| 2009/0249903 A1* | 10/2009 | Godler | F16H 19/0654 74/89.2 |
| 2012/0161579 A1 | 6/2012 | Browne et al. | |
| 2015/0152852 A1* | 6/2015 | Li | D01F 6/00 60/528 |
| 2017/0314539 A1 | 11/2017 | Kim et al. | |

FOREIGN PATENT DOCUMENTS

| | | |
|---|---|---|
| JP | 2008-89175 A | 4/2008 |
| JP | 200879371 A | 4/2008 |
| JP | 2009-258008 A | 11/2009 |
| JP | 2010-127772 A | 6/2010 |
| JP | 2015-533521 A | 11/2015 |
| WO | 2014022667 A2 | 2/2014 |
| WO | 2016064220 A1 | 4/2016 |

OTHER PUBLICATIONS

Office Action issued in corresponding Korean Application No. 10-2018-7031472, dated Dec. 19, 2019 (13 pages).

Office Action issued in corresponding Japanese Application No. 2019-508166, dated Nov. 11, 2019 (6 pages).

Office Action issued in corresponding Chinese Application No. 201780026225.6, dated Oct. 23, 2019 (6 pages).

International Search Report issued in corresponding International Application Na PCT/US2017/030199 dated Oct. 6, 2017 (4 pages).

Written Opinion of the International Searching Authority issued in corresponding International Application No. PCT/US2017/030199 dated Oct. 6, 2017 (6 pages).

Japan Notice of Allowance received in Jp Application No. 2019-508166, dated Nov. 2, 2020.

\* cited by examiner

BI-STABLE ACTUATOR DEVICES

CROSS-REFERENCE TO RELATED APPLICATIONS

This Application claims priority, pursuant to 35 U.S.C. § 119(e) to U.S. Provisional Application Nos. 62/329,803 filed on Apr. 29, 2016, and 62/350,113 filed on Jun. 14, 2016, both of which are incorporated by reference in their entirety.

BACKGROUND OF INVENTION

Thermally driven torsional actuators based on twisted polymeric and carbon nanotube (CNT) fibers and yarns have an inconvenience of being intrinsically monostable. In other words, actuators may need a continuous supply of energy to remain in an activated state. For example, if such an actuator is not utilizing any temperature changes in the environment surrounding the actuator, a continuous supply of thermal energy may be required in order to keep the actuator's temperature sufficient to remain activated. Such energy may be supplied electrically, chemically, or even photonically. Mechanical mechanisms such as latches and ratchets may be added to such thermally driven torsional actuators in order to lock the actuator in an activated position; however, the addition of such mechanisms may increase mechanical complexity of the actuator.

SUMMARY OF INVENTION

In one aspect, embodiments of the invention relate to an actuator device that includes a first actuating segment of an artificial muscle fiber, where one end of the first actuating segment is connected to a first terminal and the other end of the first actuating segment is connected to a second terminal. The device also includes a second actuating segment of an artificial muscle fiber, where one end of the second actuating segment is connected to a third terminal and the other end of the second actuating segment is connected to a fourth terminal. The device also includes a paddle disposed on both the first and second actuating segments and a heating provision disposed on the first and second actuating segments. The heating provision independently provides energy in the form of heat to the first and second actuating segments, and the actuator device moves rotates the paddle to a desired position through activating the first or second actuating segments.

In another aspect, embodiments of the invention relate to a method for manufacturing an actuator device that includes twisting an artificial muscle fiber that includes fibers and an actuating yarn guest that is operable for undergoing change in volume by a change process. The method also includes setting the artificial muscle fiber by thermally annealing the actuator material, and cutting the artificial muscle fiber into first and second actuating segments. One end of the first actuating segment is fixed to a first terminal and the other end to a second terminal, while one end of the second actuating segment is fixed to a third terminal and the other end to a fourth terminal. A paddle is disposed on both the first and second actuating segments and a heating provision is also disposed on the first and second actuating segments. The heating provision independently provides energy in the form of heat to the first and second actuating segments.

The actuator device rotates the paddle to a desired position by activating the first or second actuating segments using the heating provision. During operation, the actuator moves the load to a desired position by activating a first actuating energy in the first actuating segment, deactivating the actuating energy to the first actuating segment, and activating a second actuating energy to the second actuating segment. The amount of actuating energy required is dependent on the materials used and the environmental conditions.

Other aspects and advantages of the invention will be apparent from the following description and the appended claims.

DETAILED DESCRIPTION

Figure 1A:
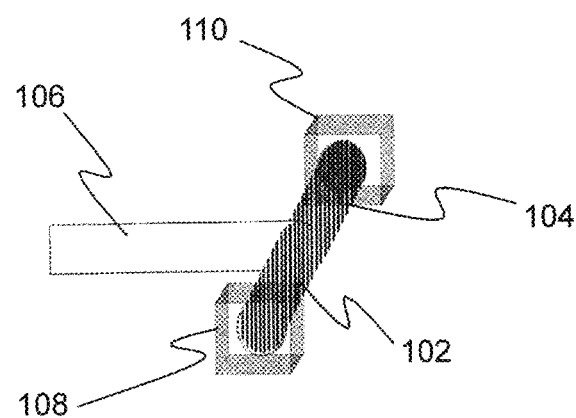
FIGS. 1A-1E are schematics in accordance with one or more embodiments of the invention.

Embodiments of the invention will now be described in detail with reference to the accompanying Figures. Like elements in the various figures may be denoted by like reference numerals for consistency. Further, in the following detailed description of embodiments of the present invention, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description.

In general, embodiments of the invention relate to an actuator device and a method of making an actuator device. Specifically, embodiments of the invention relate to an actuator geometry and sequence of activation that allows a torsional actuator based on a single twisted fiber to be bi-stable, i.e., stable in at least two different positions. One or more embodiments of the bi-stable actuator may not require any additional mechanical components. Further, one or more embodiments of the bi-stable actuator may not be affected by changes in the environmental temperature.

Thermally driven torsional/tensile actuators based on twisted fibers and nanofibers lack a latch mechanism for an activated position. In other words, such actuators require energy to remain actuated. To date, examples of thermally driven twisted/coiled actuators are mono-stable (stable only in a deactivated state).

Embodiments of the invention include actuating materials as described in U.S. patent application Ser. No. 14/610,905 filed Jan. 30, 2015, the contents of which are hereby incorporated by reference in their entirety. The simplicity of design of one or more embodiments of the invention may allow for manufacturing of complex arrays that can be attached to rigid or flexible substrates. Further, contrary to embodiments disclosed in U.S. patent application Ser. No. 14/610,905, embodiments of the invention relate to a bi-stable actuator assembly that may not require a continuous supply of energy to remain actuated.

Embodiments of the invention include actuator materials, or artificial muscles, including twist-spun nanofiber yarn and twisted polymer fibers that generate torsional and/or tensile actuation when powered electrically, photonically, thermally, chemically, by absorption, or by other means. Embodiments of the invention include actuators that utilize non-coiled or coiled yarns or polymer fibers and may be either neat or include a guest. The term "artificial muscle fiber" is generically used herein to describe the nanofiber yarn and twisted polymer fibers, or a collection (bundles) of nanofiber yarns and twisted polymer fibers that perform the actuation.

One or more embodiments of the invention may eliminate a need for electrolytes, certain counter electrodes, and/or special packaging by incorporating a solid guest material in a yarn to generate volume changes that produce tensile and torsional actuation. As used herein, the term "tensile actuation" denotes actuation in a length direction of an actuator, regardless of whether the actuator elongates or contracts in a length direction during an actuation step. For example, in hybrid nanotube actuators, twist-spun nanotubes may confine an actuating guest in both solid and molten states, and provide mechanical strength and helical geometry enabling torsional actuation and enhanced tensile actuation. Yarn actuator structures may be engineered to maximize either torsional or tensile actuation. Reversible actuation may be powered electrically, photonically, or chemically in accordance with one or more embodiments of the invention.

In one or more embodiments of the invention, high-cycle-life, large-stroke, and high-rate torsional and tensile actuators may be provided that: demonstrate a neat or hybrid twist-spun nanotube yarn as an actuating element; require no electrolytes or counter-electrodes and operate at low voltages; may be electrically, chemically, and photonically powered; and/or provide 7.3% tensile contraction while lifting heavy loads at extreme temperatures where no other high work capacity actuator can survive.

Embodiments of the invention may provide torsional and tensile actuation for neat twist-spun nanotube yarns that are electrothermally heated to incandescent temperatures.

In one or more embodiments, complex coiled fiber geometries may be used to increase actuator performance. Paraffin waxes may be used in some embodiments as prototypical guests in carbon nanotube yarns because of high thermal stability, tunability of transition widths and temperatures, large volume changes associated with phase transitions and thermal expansion, and their ability to wet carbon nanotubes.

In one or more embodiments of the invention, twist insertion and optional fiber coiling may be applied to ordinary polymer fibers, for example, high strength polyethylene and nylon used for fishing line and sewing thread, in order to obtain high performance actuators that provide torsional actuation, tensile actuation, or a combination thereof. In some embodiments, the need for electrolyte, counter electrode, and special packaging may be eliminated because electrochemical processes are not required for actuation and reversible actuation can be powered electrically, photonically, thermally, or chemically for twisted and coiled polymer fibers.

Both cost and performance provide major advantages for twisted and coiled polymer fibers in accordance with one or more embodiments of the invention. Commercially available polymer fibers as a precursor to the polymer actuators are relatively inexpensive. The processes needed to convert commercially fibers to actuators (twist insertion and optional incorporation of conductor) are also inexpensive in accordance with one or more embodiments of the invention.

Actuation of hybrid yarns by electrically, chemically, and photonically powered dimensional changes of yarn guest generates torsional rotation and contraction of the helical yarn host in accordance with one or more embodiments of the invention.

One or more embodiments of the invention include a twist-spun nanofiber yarn. For the purpose of this disclosure, "nanofibers" are defined as fibers that have smallest lateral of below 1000 nm. Networks of electrically interconnected nanofibers having predominately smallest nanofiber lateral dimensions of either below 100 nm or below 10 nm may be especially useful for different embodiments. Nanoribbons may be considered a specific type of nanofibers.

In accordance with one or more embodiments of the invention, the actuator material comprises a network of twist-spun nanofibers that is in the form of a yarn or a material comprising a twist-spun nanofiber yarn, such as a woven textile or a braided or plied twist-spun yarn. Various nanofibers and nanofiber syntheses and fabrication processes can be used, as can mixtures of different nanofiber types and mixtures of nanofibers with other materials. As one example, especially for hybrid actuating yarns, oriented nanofibers produced by electrostatic spinning may be twist-spun into yarns either during or after electrostatic spinning. As another example, nanotubes in forest drawn carbon nanotube sheets may be coated with another material as a template (such as a ceramic or metal), and then twist-spun to make an actuating yarn (which may be infiltrated with a guest to make a hybrid actuating yarn). Depending upon the intended actuator deployment, the nanotube template for this process can optionally be removed either before or after twist spinning.

Embodiment of the invention generally relate to an apparatus for rotating a device/object about an axis using artificial muscle actuators. The apparatus may precisely control the rotation rate of a device/object attached to the artificial muscles through controlled heating of the artificial muscles.

Embodiments of the invention include a paddle, which may have the device/object mounted on it, suspended by artificial muscles. The artificial muscles rotate upon the application of heat, which may be provided by a small wire wound around the individual muscles that make up the artificial muscle. For example, electric current may be passed through the wire, causing the wire to heat up due to the resistance of the wire. The speed of angular rotation of the paddle may be controlled by varying the current supplied to the copper wire and thus varying the heat provided to the artificial muscles. In other embodiments, the muscle may be composed of a conductive material and the electricity may be applied directly through the conducting material in the artificial muscles.

Embodiments of the invention may be designed to rotate a paddle at any desired speed, which may be desired to be held constant or may vary with time. Embodiments also include an apparatus that incorporates electronics that may sense an angular rotation rate of the paddle to which the device/object is attached. These electronics may also automatically adjust the rate of angular rotation.

Embodiments of the invention may incorporate a mechanism to restrict motion of a paddle to which the device/object is attached. Such embodiments may provide a constant range of motion. In addition, the set of angles through which the paddle rotates may be controlled by manually rotating terminals at either end of the apparatus. The terminals may also be turned by other means, such as motors or other artificial muscle fibers.

Embodiments of the invention may provide advantages in terms of cost of production, silence, control, simplicity, replace-ability, svelte design, and ease of mass production. Embodiments of the invention may have all of the advantages over motors discussed above, with some added benefits as disclosed herein.

FIG. 1 shows an actuator device in accordance with one or more embodiments of the invention. These embodiments include a bi-stable actuator that includes two segments of actuator material with a load disposed between the at least two segments. In FIG. 1A, a paddle 106 is the load and the paddle 106 is in a stable position and a first segment 102 and a second segment 104 are in a non-actuated state. As shown in FIG. 1, one end of a first segment 102 may be fixed to a first end piece 108, while one end of a second segment 104 is fixed to a second end piece 110.

Figure 1B:
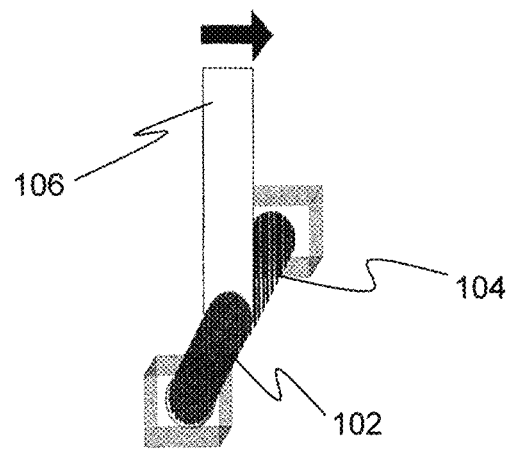
Figure 1C:
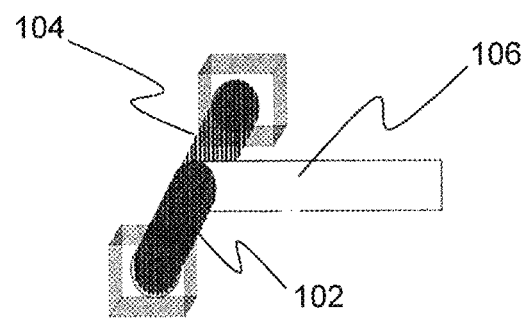
Figure 1D:
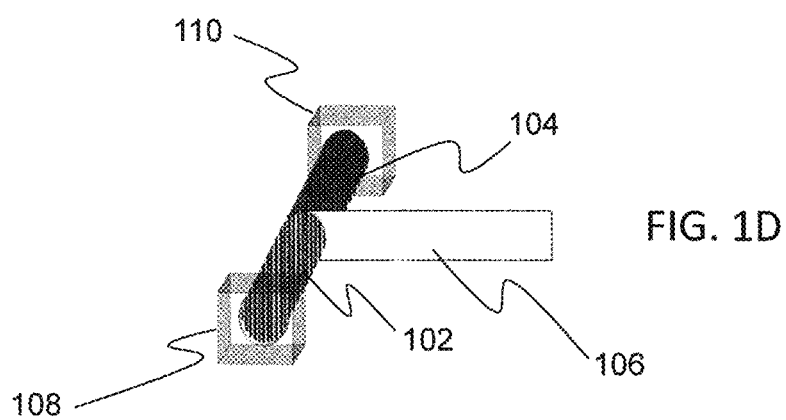
Figure 1E:
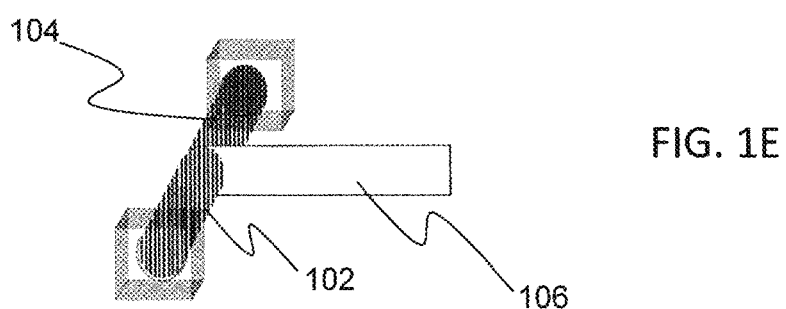

During actuation, as shown in FIG. 1B, the first segment 102 is activated by supplying an actuating energy, which causes the paddle 106 to move (rotate). In this configuration, the first segment 102 untwists, while the second segment 104 uptwists. In FIG. 1C, the paddle 106 reaches the desired position. Then, in FIG. 1D, the front segment 102 is deactivated by removing the actuating energy and the second segment 104 is briefly activated by supplying an actuating energy, which allows the second segment 104 to deform and lose torque on the paddle. This results in the paddle 106 being in a second stable state, as shown in FIG. 1E.

As a specific example, in the embodiments disclosed in FIG. 1, a 15 V, 60 mA current may be used to supply the actuating energy electrically to the device in accordance with one or more embodiments of the invention. In this example, the paddle weighs 50 mg, while the actuating segments weigh 3.7 mg.

One of ordinary skill in the art will appreciate the number of applications that may benefit from embodiments of the invention. One or more embodiments of the invention may be used for shutter and/or blinds control for houses or structures. For example, one or more embodiments of the invention may be used for an automatic blind system where the presence of direct sunlight heats up the actuating material causing them to adjust the blinds. Such applications may also be used to direct solar panels for efficient collection.

One or more embodiments of the invention may be used to direct air flow through vents by valve control. The lack of noise associated with the actuation may make one or more embodiments of the invention desirable. Further, one or more embodiments of the invention may be used for opening doors, lids, or hatches on houses, and appliances, based on a variety of triggering events.

One or more embodiments of the invention may be designed to cooperate with additional sensors, for example motion, smoke, or carbon monoxide detectors, and designed to actuate in response to such sensors.

In the embodiments described by FIG. 1, the paddle 106 is shown with a planar shape where the plane is perpendicular to the first segment 102 and the second segment 104; however, these embodiments are not limited as such. For example, the paddle may have a planar surface that is orientated parallel, or in the same direction as, the first segment and the second segment. In such embodiments, the paddle may act as a mounting surface where the actuation of the device causes the surface of the paddle to tilt and/or spin.

Figure 2:
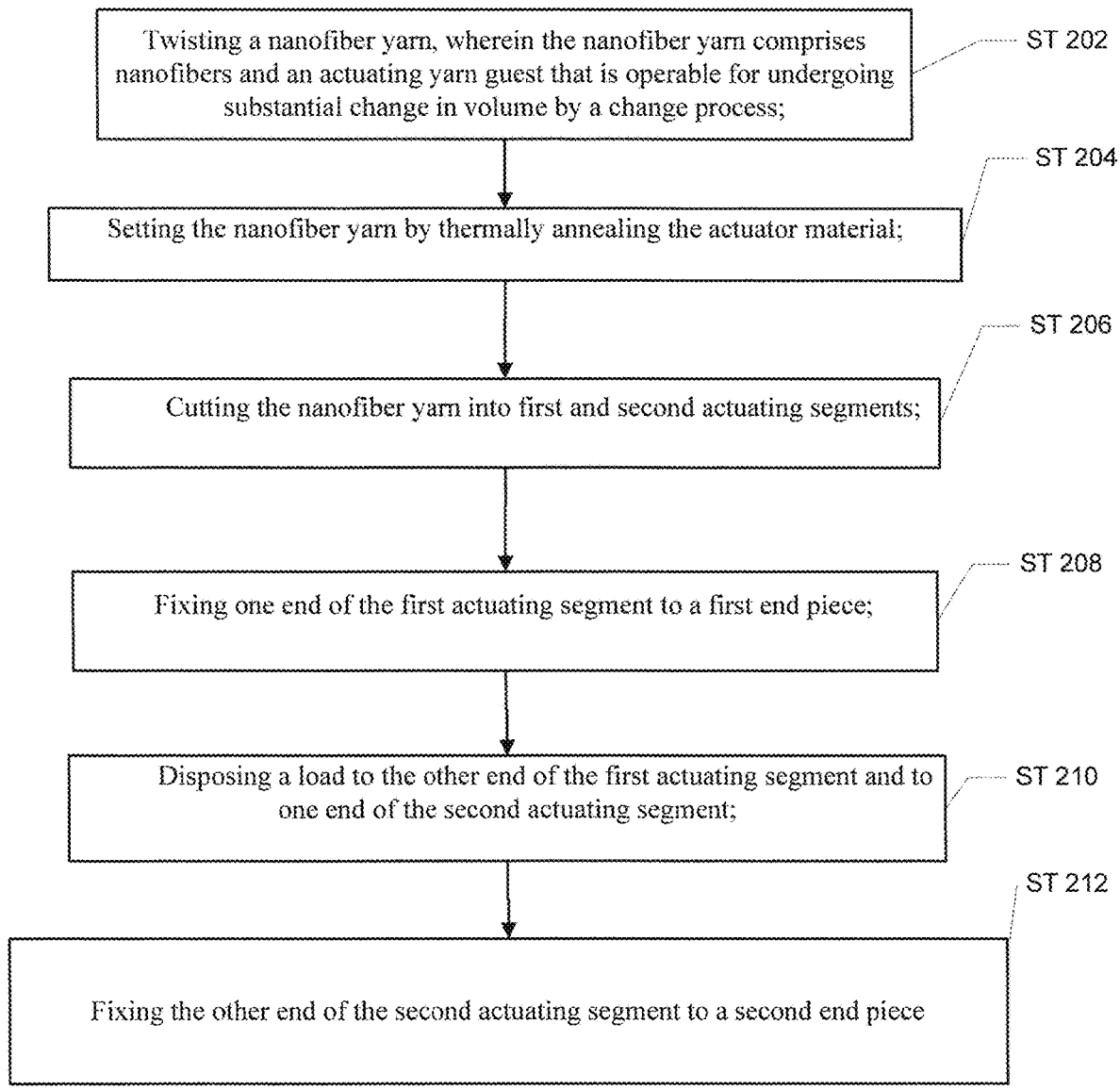
FIG. 2 is a flow chart in accordance with one or more embodiments of the invention.

FIG. 2 is a flow chart demonstrating methods for manufacturing an actuator described by FIG. 1 in accordance with one or more embodiments of the invention. First, an actuator material is fabricated as described in U.S. patent application Ser. No. 14/610,905. For example, in step 202, a nanofiber yarn is twisted, wherein the nanofiber yarn includes nanofibers and an actuating material that is operable for undergoing substantial change in volume. Then, in step 204, the nanofiber yarn is set by thermally annealing the nanofibers and actuator material.

In step 206, the nanofiber yarn is cut into first and second actuating segments. In step 208, one end of the first actuating segment is fixed to a first end piece. In step 210, a paddle is disposed to the other end of the first actuating segment and to one end of the second actuating segment. A paddle may be disposed by any known means, for example, epoxy. The other end of the second actuating segment is fixed to a second end piece in step 212.

In one or more embodiments of the invention, a heating provision may be incorporated into the nanofiber yarn with the actuator material. For example, a conducting wire may be wrapped around the actuator material, or a coating may be applied to actuator material. By incorporating the electrically conductive material, the actuating material may be heated using an applied electrical current. The heat provided is used as the actuating energy. The incorporation of the heating provision for a thermal process may be performed prior to cutting the nanofiber yarn into first and second actuating segments.

Further, in one or more embodiments of the invention, first and second independent electrical connections may be established to the first and second actuating segments, respectively. This may be established by three electrical connections to the actuating device, two connections to each of the first and second actuating segments and one connection to both, for example at the paddle.

One of ordinary skill in the art, in view of this disclosure, will appreciate that the size and characteristics of the actuation will be determined by the characteristics of the actuating material. For example, the width and length of the first segment helps determine the amount of torque on the paddle.

For example, a nylon 6 twisted monofilament 0.86 mm thick may be manufactured as described in FIG. 2. Such actuators may be manufactured by twisting nylon monofilament fishing line rated for 801b under the weight of 1 Kg until the point of coiling. The fibers may then be firmly tether and treated at 150 C for 10 min in order to fix the fiber twisted. A 40 AWG copper wire may be used as a conducting material. The twisted fibers may be wrapped with the copper wire leaving a space of 0.2 mm between the wires. Flat stainless wire may be used for attaching the actuator segments to the substrate (end pieces) and to the paddles. The flat stainless wire may be compressed around the twisted and copper wrapped fibers in order to provide the mechanical and electrical connection.

Figure 3:
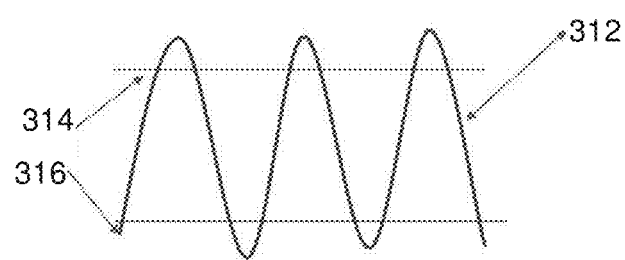
FIG. 3 is a chart in accordance with one or more embodiments of the invention.

In one or more embodiments of the invention, the paddle motion may be controlled in terms of range of motion and rate of motion. In embodiments disclosed herein, the range of motion may be controlled using mechanical or electrical stops. For example, for oscillating motion as described in FIG. 3, the artificial muscles may be engineered to oscillate in motion described by the curve 312. Desired stops may be engineered as demonstrated by the lines 314, 316. The stops 314, 316 may be mechanical or electrical in nature in accordance with embodiments herein. For example, the device may be positioned such that the environment may limit the motion of the paddle as shown in FIG. 1. In other embodiments, a simple mechanical stop may be positioned to stop the motion of the paddle.

Figure 4:
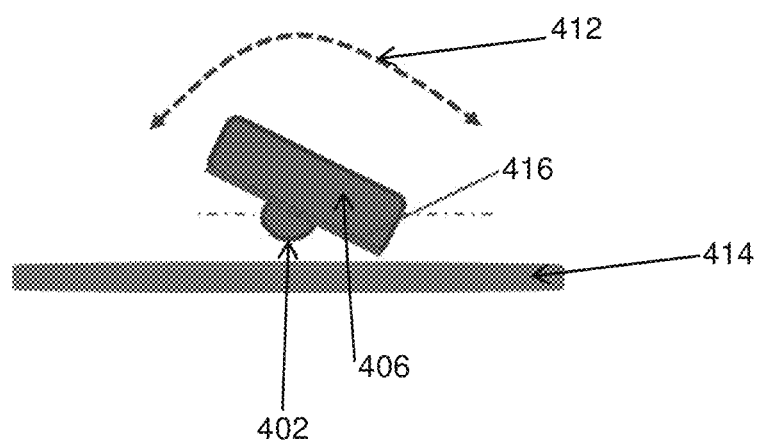
FIG. 4 is a schematic in accordance with one or more embodiments of the invention.

FIG. 4 demonstrates a configuration for an electrical stop as described above. In FIG. 4, the plane of the paddle 406 is parallel to the artificial muscle fibers 402, and the desired range of motion is described by the line 412. These embodiments include a conductive material 414, such as a pin, rod, foil, paper, tape, and/or textile. These embodiments also include a conductive line 416 connected to the surface of the artificial muscle bundle 402, or connected to the conductive material included in the artificial muscle 402. In such embodiments, the paddle motion 412 may be controlled by a power supply (not shown). For example, the electrical contact may be engineered to stop the motion when the conductive line 416 makes electrical contact with the conducting material 414. In one or more embodiments, the device may be engineered such that, when there is electrical contact, the muscle will change direction and move in the opposite direction without overshooting. In one or more embodiments, a feedback loop can be used to monitor and compensate for (if necessary) the position of the paddle.

Figure 5:
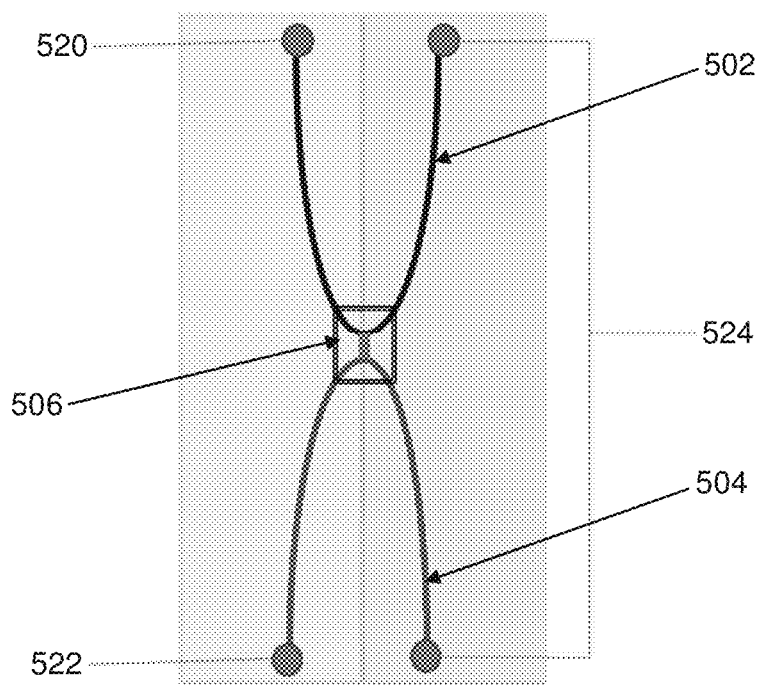
FIG. 5 is a schematic in accordance with one or more embodiments of the invention.

FIG. 5 demonstrates a configuration in accordance with one or more embodiments disclosed herein. The embodiments disclosed in FIG. 5 include a first artificial muscle fiber bundle 502 and a second artificial muscle fiber bundle 504. The artificial muscle fibers 502, 504 do not come into direct contact with each other and instead there may be a piece of material that connects the two muscles mechanically but maintains their separation electrically. In some embodiments, the piece of material may be a paddle 506; however, embodiments are not limited as such. As shown in FIG. 5, power is supplied through the terminals 520, 522. The current travels through the artificial muscle to a single ground terminal 524 ground on the other side.

In the embodiments described by FIG. 5, an electrical current is passed through terminal 520 causing the artificial muscle 502 to rotate, which rotates the paddle 506. After the paddle has reached the end of its desired angular rotation, the artificial muscle 502 is deactivated, and the artificial muscle 504 is activated through the terminal 522 to start rotation in the opposite direction.

Figure 6:
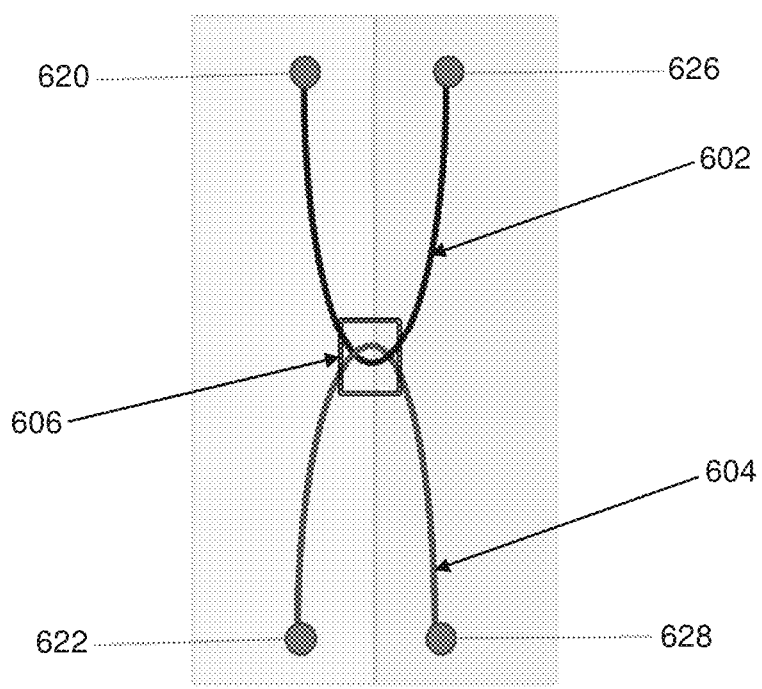
FIG. 6 is a schematic in accordance with one or more embodiments of the invention.

FIG. 6 demonstrates another configuration in accordance with one or more embodiments disclosed herein. The embodiments disclosed in FIG. 6 include a first artificial muscle fiber bundle 602 and a second artificial muscle fiber bundle 604. The artificial muscle fibers 602, 604 come into direct contact with each other. There may be a piece of material that connects the two muscles mechanically. As in previous embodiments, the piece of material may be a paddle 606; however, embodiments are not limited as such. As shown in FIG. 6, power is supplied through the terminals 620, 622, and the terminals 626, 628 are each connected to ground and capable of being disconnected.

In the embodiments described in FIG. 6, the terminal 628 is disconnected from ground so that artificial muscle fiber bundle 604 connection to ground is switched off. Electrical current is passed through artificial muscle fiber bundle 602, causing artificial muscle fiber bundle 602 to rotate, which rotates the paddle 606. After the paddle 606 has reached the end of its desired angular rotation, the terminal connection 626 is deactivated, or disconnected from ground. The artificial muscle fiber bundle 604 is then activated to start rotation in the opposite direction. The artificial muscle fiber bundle 604 is activated by connecting terminal 628 to ground and supplying an electrical current through terminal 622.

The embodiments of FIG. 6 may have the advantage of not requiring as much insulation to isolate the artificial muscle fiber bundles, but these embodiments may require electronics to account for current leaking into the artificial muscle fiber opposite from the artificial muscle fiber desired to be activated.

If both the terminals 626, 628 are connected to ground, the currently supplied through terminal 620 to activate artificial muscle fiber bundle 602 will also leak to the artificial muscle fiber bundle 604. This activation of the opposite muscle may make the entire process 50% less efficient, because the opposite muscle directly opposes the motion of the activated muscle. Thus, the terminals 626, 628 must be separately connectable to ground. In one or more embodiments, this may be achieved through the use of electronic switches.

Embodiments disclosed here in may have a controlled angular rotation rate. In one or more embodiments, the applied voltage is varied to provide a steady angular rotation rate. The change in voltage affects the current flow and, thus, the heat generated to actuate the artificial muscles. In one or more embodiments, a Pulse Width Modulation (PWM) modulating the voltage at a high frequency is used in a manner that the peaks and troughs between the square modulation waves average out to the desired value. By controlling the width of the square waves the average applied current may be controlled and the muscle may be heated at a desired rate. A specific heating rate will lead to a specific rotation rate.

Figure 7:
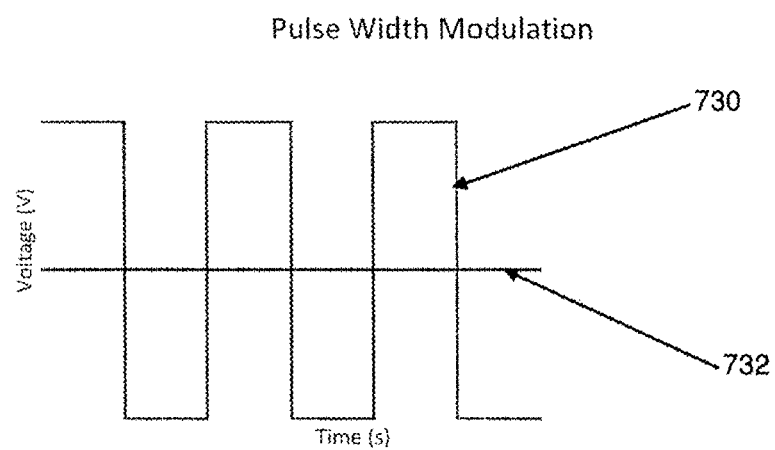
FIG. 7 is a chart in accordance with one or more embodiments of the invention.

For example, as demonstrated in FIG. 7, the applied voltage 730 may be a square modulated voltage such that the average voltage 732 of the applied voltage 730 is the voltage required to activate the artificial muscle actuator. The pulse width and frequency of the modulation provides the specific heating rate which leads to a specific rotation rate of the actuator. For example, the voltage may be 12 V modulated with a frequency of 900-1000 Hz. More specifically, the voltage may be modulated at 980 Hz. The width of the modulation may vary from 10 to 50%, depending on the artificial muscle fibers load, the ambient temperature, the internal resistance of the artificial muscle fibers, etc.

Figure 8:
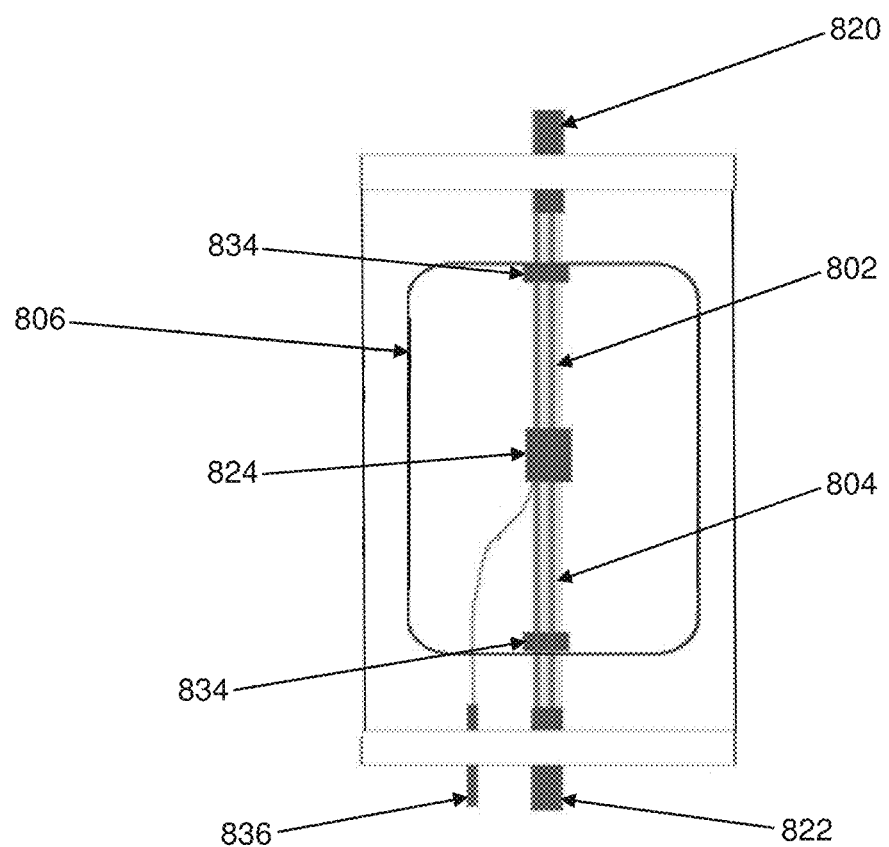
FIG. 8 is a schematic in accordance with one or more embodiments of the invention.

FIG. 8 demonstrates a device in accordance with one or more embodiments of the invention. Embodiments described by FIG. 8 include a rotating platform 806 (for example, a paddle or guide plate), a first artificial muscle bundle 802, and a second artificial muscle bundle 804. The first artificial bundle 802 is electrically connected between the terminal 820 and the common terminal 824, while the second artificial muscle bundle is electrically connected between the terminal 822 and the common terminal 824. The rotating platform 806 is positioned at the common terminal 824. In these embodiments, the first and second artificial muscles 802, 804 may include one or more artificial muscles fibers or artificial muscle fiber bundles that are bound together at various points in the apparatus. These embodiments may also include guide bearings 834. The guiding bearings 834 may be added around the muscles in order to give stability to the rotating platform 806. The guide bearings 834 may be attached to the paddle and allow the artificial muscle bundles to freely rotate inside of the guide bearings 834. The embodiments described by FIG. 8 may also include a sensor apparatus 836. The sensor apparatus 836 is provided to detect the angle of the rotating platform 806.

As in previous embodiments, embodiments include each artificial muscle is caused to rotate by the application of heat. For some of these muscles the heat is provided by resistance from an electric current passing through a thin conductive layer/wire/element and/or heating element around the muscle fiber. Other artificial muscles in the bundle may not have any electrically conductive material wound around them and, thus, these artificial muscles obtain heat by absorbing heat from neighboring muscles which are made electrically conductive. The speed of angular rotation may be controlled by varying the current supplied to the conductive layer and, thus, varying the heat provided to the artificial muscles. Alternatively, all of the artificial muscles may be include conductive material and the electricity may be applied directly through them.

In the embodiments described by FIG. 8, a voltage is applied across terminal 820 through to the common grounding terminal 824 in the center of the apparatus. This causes the first artificial muscle bundle 802 with a voltage applied to heat and activate, causing rotation of the rotating platform 806. When the desired angle is achieved, the voltage is removed from terminal 820 and a voltage is applied to terminal 822 so that the second artificial muscle bundle 804 activates. Once activated, the second artificial muscle bundle 804 causes rotation of the rotating platform 806 in the opposite direction.

As described above, the voltage applied may be varied so that the effective amount of current flowing through the muscles is controlled. The Pulse-Width Modulation (PWM) described above may be particularly useful in situations where only a specified voltage is available. The angular rotation rate may be set to have a specific rate or it may be set to vary based on the specific application demands.

In these embodiments, the apparatus may function as a Bi-Stable artificial muscle, where one of the first or second artificial muscle bundle is heated to cause the rotating platform 806 to lock into position. This may be particularly useful for situations where it is necessary to stop the rotation of the rotating platform 806, without consuming electricity.

Figure 9:
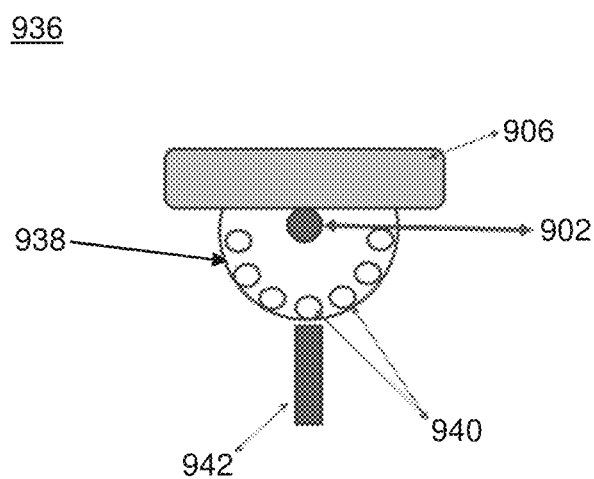
FIG. 9 is a schematic in accordance with one or more embodiments of the invention.

FIG. 9 demonstrates an embodiment of a sensor apparatus in accordance with one or more embodiments of the invention. The sensor apparatus 936 includes an encoder 938 that may be attached to the paddle 906 and enclosing the artificial muscle fibers 902. The encoder 938 may include holes 940. A sensor 942 is used to detect the position of the encoder 938 using the holes 940. As such, the angular position of the paddle 906 may be determined.

In other embodiments, the position of the paddle may be determined by variation of the internal resistance of the artificial muscle fiber due to the change of the degree of twist of the actuator during torsional.

Embodiments disclosed here in also include an actuator device for 2-D angular rotation, providing the ability for the paddle to rotate in a circular angular fashion. For example, the embodiments disclosed in FIG. 6 may be modified to include addition artificial muscle fiber bundles essentially perpendicular to the artificial muscle fibers shown in FIG. 6. In such embodiments, alternating layers of insulating material may be used to prevent the muscles electrically contacting. The paddle may be designed to prevent undesirable contact between the paddle edge and the muscle fiber when the paddle is rotated. That is, the paddle may be designed so that the paddle edge does not touch the artificial muscles perpendicular to the muscle being activated.

In embodiments disclosed herein, the artificial muscle fibers may be attached and connected in a variety of fashions. For example, for conducting connections, a stainless, copper, brass, or other malleable flat metal may be used to firmly fix (clamp) the muscle and conduct electrical current. In some embodiments, a metal tube may be used. The artificial muscle fibers may be inserted into a metal tube and compressed around the muscle or bundle. In other embodiments, a conductive epoxy may be used.

Because of their strength, electrical conductivity, and mechanical strength, carbon nanotubes (CNTs) may be used in the actuating material in accordance with one or more embodiments of the invention. Useful types of CNTs include carbon multiwalled nanotubes (MWNTs), carbon fewwalled nanotubes (FWNTs), and carbon single-walled nanotubes (SWNTs). Such SWNTs and FWNTs may be useful even when the nanotube diameter is sufficiently large that the SWNTs or FWNTs collapse into ribbons.

Twist-spun nanofiber yarns that comprise nanoribbons of graphene sheets may be used in accordance with one or more embodiments of the invention. One method for making these graphene ribbons as high-aspect ratio nanofibers is by unzipping carbon nanotubes. This unzipping process may be accomplished either before or after a CNT array (such as a CNT sheet) is twist-spun into a yarn.

Both solid-state and liquid-state processing methods may be used to produce twisted nanofiber yarns in accordance with one or more embodiments of the invention. Some examples of useful solution spinning methods are polymer-coagulation-based spinning and solution-based spinning methods that do not involve a polymer coagulant. To provide twisted nanofiber yarns, yarn twist must be inserted during or after yarn solution spinning.

In accordance with one or more embodiments, for solution spinning using coagulants (such as a polymer) that remain in the yarn after solution spinning, it is typically useful to remove these coagulants before using these yarns to make twist-spun yarns.

Because of these complications in using solution spinning to make twisted yarns, as well as CNT length degradation during CNT dispersion for solution spinning, chemical vapor deposition methods that directly result in nanotube assemblies suitable for spinning may be used in one or more embodiments. Such spinning methods that do not involve dispersion of CNTs in a liquid are referred to as solid-state spinning, whether or not liquids are deployed during or after processing. The resulting yarns may be generally stronger and able to accommodate higher twist insertion than neat yarns derived by solution spinning.

One such solid-state spinning method involves chemical vapor deposition (CVD) synthesis of nanotubes using a floating catalyst and subsequent yarn draw a twist insertion into a collected CNT aerogel. Other methods of twist-based spinning involve twist insertion into a nanotube aerogel sheet that has been drawn from a nanotube forest that has been synthesized on a substrate by CVD. Such twist insertion can be either during sheet draw from a CNT forest or after a sheet or sheet stack has been drawn from a CNT forest.

One or more embodiments of the actuator segments may be fabricated using the following methods to make twist-spun non-coiled and coiled CNT yarns. Drawable carbon MWNT forests for producing twist-spun yarns are grown by chemical vapor deposition on silicon wafers coated by iron catalyst using acetylene ($C_2H_2$) gas as the carbon precursor. Transmission and scanning electron microscope (SEM) images of approximately 350 μm high forests indicate that MWNTs may have an outer diameter of approximately 9 nm, contain about 6 walls, and form large bundles. Thermogravimetric analysis indicates that the amount of non-combustible material in the drawn nanotubes may be below 1 wt %, which may provide an upper limit on the amount of residual catalyst.

Small and large diameter yarns may be fabricated in which twist insertion result in three different scroll geometries: Fermat, Archimedean, and dual-Archimedean. Small diameter yarns may be made by symmetrical twist insertion during sheet draw from a forest or into a pre-drawn nanotube sheet suspended between either a forest and one rigid end support or two rigid end supports. Because of differences in end constraints, these methods may provide Fermat scrolls for the former cases of sheets connected to a forest and dual-Archimedean scrolls for the latter case, where two rigid rod supports are used. The yarn diameter may be varied from about 10 µm to about 30 µm by changing the drawn forest width from about 0.5 cm to about 5 cm. Much larger diameter dual-Archimedean yarns may be fabricated by stacking 20 to 40 MWNT sheets (1.0 cm to 2.5 cm wide and 5 to 17 cm long) between rigid rods and inserting twist using an electric motor, while one end of the sheet stack supports a 5 g weight tethered to prohibit rotation. In one or more embodiments, approximately 150 turns are necessary to collapse a 5 cm long 30 sheet stack into a 4.5 cm long yarn having dual-Archimedean structure. Introduction of asymmetric stress during twist insertion may convert these Fermat and dual-Archimedean yarns to Archimedean yarns.

In accordance with one or more embodiments, Fermat yarns directly spun during sheet draw from a forest may be used for immersion driven torsional actuation, polydiacetylene hybrid yarn actuators, two-ply yarn actuators, and nonplied, wax-filled torsional actuators. Such Fermat yarns may be fabricated by drawing a length of nanotube sheet from a forest, and then inserting twist into one end of the sheet via a motor and a rigid support, while allowing the other end to freely draw from the MWNT forest. Unless otherwise noted, inserted twist may be normalized with respect to the final yarn length. For other instances, where in most cases twist was inserted in a sheet stack to form a dual-Archimedean yarn, twist may be normalized to the length of the sheet stack.

According to the direction of twist insertion, yarns may be classified as S or Z yarns (for clockwise and anticlockwise twist insertion, respectively). If all segments in a yarn have the same chirality at corresponding structural levels, the yarn may be considered homochiral. This means, for instance, that a SZ two ply yarn (with S twist due to plying and Z twist within each ply) is homochiral. If the yarn has segments having different chirality at a same structural level, then the yarn is called heterochiral. For heterochiral yarns, different chirality yarn segments may be essentially a mirror image of each other.

The presently used term "inserted twist" (which is sometimes called linking number) is the sum of internal yarn twist and the twist due to coiling. As done for other structural terms, "yarn diameter" refers to the diameter of the component yarn even when it is within a coiled or plied structure, and is thereby differentiated from the "coiled yarn diameter" or the "plied yarn diameter".

Over-twisting MWNT yarns, as for ordinary textile yarns, rubber bands, and DNA molecules, causes coiling (which may be referred to as "writhe"). Such coiling, as well as coiling in plied yarn, may be used to dramatically amplify tensile stroke and work capabilities compared with those for uncoiled yarn. Coiled yarns may be fabricated under constant load from non-coiled, twist-spun yarns by inserting additional twist until a yarn is contracted to 30-40% of its original length. For a dual-Archimedean yarn made under 4 g load by twist insertion in a stack of 40 co-oriented, 9 mm wide, 15 cm long sheets, coiling may start at approximately 580 turns and the yarn may be completely coiled after approximately 620 turns. Twist insertion until complete coiling may produce a 60% contraction in yarn length.

The term coiled yarn is used herein to generically refer to a yarn that has at least an approximately helical shape in some yarn portions, whether or not this coiling is a result of simple yarn overtwist or such processes as yarn plying.

Depending upon application needs, nanofiber sheets used for fabrication of twistspun nanofiber yarns may be optionally densified before twist insertion. Further, the nanofiber yarns produced by twist spinning can optionally be densified after or during twist insertion. A particularly convenient method for causing sheet densification is by using surface tension effects due to the process of liquid infiltration and subsequent liquid evaporation.

Electrospinning of nanofibers, and especially polymer nanofibers, may provide a useful alternative route to twist-spun nanofiber yarns that provide useful hosts for hybrid yarn actuators in accordance with one or more embodiments of the invention. In one embodiment, nanofibers may be first electrospun into oriented sheets of nanofibers using known electrospinning methods. As with carbon nanotube sheets, these nanofiber sheets can be twist-spun into yarns. Guests used for carbon nanotube actuators can be provided within the host yarn either by guest deposition on the sheets before twist spinning or by incorporation of the guest after twist spinning.

Various known methods of twist insertion may be used for introducing twist during spinning into yarns in accordance with one or more embodiments. Such methods include, but are not limited to, ring spinning, mule spinning, cap spinning, open-end spinning, vortex spinning, and false twist spinning technologies.

Twist-spun yarns that comprise nanofibers may be useful for selected embodiments. Giant interfacial energies that arise may enable convenient confinement of molten guest in a hybrid yarn actuator. For example, molten wax in an actuated wax-filled yarn may undergo a fractional volume decrease when cooled. If this wax volume change occurred without decreasing yarn volume, nanotube-paraffin interfacial energies would be replaced by nanotube-air interfacial energies at an energy cost of the gravimetric surface area of the nanotubes. During subsequent yarn actuation by heating and corresponding wax expansion, this elastic energy in the yarn may be progressively released, thereby maintaining coincidence between molten wax and yarn volume over the entire actuation cycle. Thus, excess wax on the yarn surface, as well as wax evaporation, may decrease tensile stroke.

Both very large and very small diameter twisted nanofiber yarns may be used in accordance with embodiments of the invention. However, the load carrying capabilities of nanofiber yarns generally increase with increasing yarn diameter. Single-ply carbon nanotube yarn diameters of 4 µm to 50 µm may be directly twist-spun from 400 µm high carbon nanotube forests, and increasing forest height and increasing forest density increases the yarn diameter obtainable by spinning a given width of forest. Sheets from 400 µm high carbon nanotube forests may be pre-drawn, stacked, and then twist-spun to produce single-ply yarns having a several hundred micron diameter. These diameters may be dramatically increased by yarn plying and by guest incorporation prior to twist insertion.

By using specialized techniques, carbon nanotube yarn diameters down to 100 nm may be twist-spun from carbon nanotube forests. For micron scale and smaller scale applications, the self-twisting of two nanowires may produce a nanoscale plied yarn structure.

Embodiments of the invention may be subjected to at least 30 initial training cycles in order to stabilize the structure of the hybrid yarn, and thereby enable highly reversible operation during subsequent evaluation for over 2 million reversible actuation cycles.

Methods for incorporating guest actuating material into a host yarn in accordance with one or more embodiments include, for example, melt and solution infiltration (which can be followed by in-situ polymerization) and biscrolling, where the guest is deposited on a MWNT sheet before twist insertion. Paraffin waxes may be used as guests because of high thermal stability, the tunability of transition widths and temperatures, the large volume changes associated with phase transitions and thermal expansion, and their ability to wet carbon nanotube yarns.

Liquid state and quasi-liquid-state guest deposition may also be used, such as electrophoretic deposition, solution filtration-based deposition using the nanotube sheet stack as a filter to capture guest nanoparticles, drop casting, and ink-jet printing.

In one or more embodiments, selection of volume changing guests for thermally, electrothermally, and photothermally powered actuators may be made depending upon volume changes due to solid-state phase transitions, solid-melt phase transitions, and solid-state and liquid-state thermal expansion coefficients in temperature regions removed from phase transition regions. Paraffin waxes may provide the advantage that both the temperature and sharpness of thermal-dimensional changes are highly tunable. Further, these waxes are non-toxic. Other long chain molecules, like polyethylene glycols and fatty acids can also be usefully deployed. These molecules, and like molecules that are deployable for thermal energy storage, may be used as guests in twist-spun actuators because high enthalpies of phase transition are usually associated with large volume changes. Organic rotator crystals (of which some of these long chain molecules may be classified) are useful because rotational disorder is introduced by solid-state transitions that can have large associated volume changes. Because of low volatility, plastic crystals that are ionic crystals may be useful. One example for actuation at relatively low temperatures is tetraethylammonium dicyanamide, which may undergo a sharp 5.7% volume expansion at a solid-state phase transition that occurs between 17 and 20° C.

In applications of one or more embodiments where the guest material may be prepared in liquid form and later solidified, it may be useful to infiltrate the nanofiber yarn when it still has a low degree of inserted twist. This may be advantageous because the low-twist nanofiber yarn is still not fully densified by twist insertion, so there may be a relatively large amount of void volume between the nanofibers. This large void volume (measured as percent of total yarn volume) may enable the incorporation of a large volume percent of yarn guest, thereby amplifying actuation. This low-twist-infiltration method may be applied, for example, to nanofiber yarn guest that is imbibed into the twisted nanofiber yarn as a precursor liquid resin, and then polymerized, or to a polymer or polymer mixture that is infiltrated into a twisted nanofiber yarn while in the molten state and then solidified. After the resin cure or polymer solidification, if the guest-filled yarn still retains sufficient flexibility, more twist may be applied to the obtained hybrid yarn in order to fully coil it. If the guest material is applied after coiling the host nanofiber yarn, much less void space would be available in the yarn and therefore less guest material can be incorporated. Dual-Archimedean yarns containing 95% of silicone rubber may be prepared in this way.

In one or more embodiments, silicone rubber may be used as a suitable guest material for tensile actuators based on hybrid yarns because it has a wide working temperature range (−55° C. to 300° C.) and a large linear thermal expansion ($3 \times 10^{-4}$/K) for thermal, electrothermal, or photothermal actuation. Due to the high volume percent of guest material that can be incorporated using this low-twist-infiltration method, very large actuator strokes may be obtained. Using this low-twist-infiltration method, up to 34% tensile contraction under 5 MPa tensile load may be obtained for electrical pulse heating of a coiled carbon nanotube yarn containing silicone rubber guest.

In one or more embodiments, hybrid nanofiber yarn actuators may be optionally made by the process of (a) inserting less twist than required for coiling, (b) infiltrating a molten polymer or an uncured polymer resin, (c) solidifying the polymer or curing the polymer resin and (d) inserting twist sufficient to cause yarn coiling. In fact, the twist inserted before infiltrating a molten polymer or an uncured polymer resin can be all or mostly false twist, e.g., obtained by twisting in one direction and then untwisting in the opposite direction.

The above assumptions of equal length yarn segments and the location of load (or paddle) at either yarn midpoint or yarn end were made to avoid any unnecessary complexity for the above discussion. Depending upon the application needs, the load need not be at yarn center. In fact, in some applications such as those demonstrated in FIG. 1, multiple paddles may be deployed along the yarn length.

Additionally, because unactuated yarn lengths may serve in many cases as torsional return springs, these unactuated yarn lengths can be replaced by torsional return springs made of various materials, including yarns or fibers that do not comprise nanofibers. For cases where different yarn segments are actuated, these yarn segments need not have opposite chirality or be even made of the same material.

One or more embodiments of the invention may advantageously provide great energy savings and reduction of mechanical complexity for torsional, thermally driven actuators. Embodiments of the invention may be potentially extended to more than 2 stable states. One or more embodiments of the invention may be insensitive to changes of environmental temperature.

Embodiments of the invention may have applications in thermal regulation, for example, switching a surface from absorbing to reflective. Embodiments of the invention may be used to adjust solar cells relative to sunlight for improving absorption. Embodiments of the invention may also have applications in surface cleaning, for example changing from a hydrophobic surface to a hydrophilic surface. Embodiments of the invention may also have applications in camouflage for military application. One of ordinary skill in the art will appreciate that actuators have applications in many industries and may even be used for decorative purposes or in fashion.

As described with respect to FIG. 8, one or more embodiments may include a guide plate-type paddle. The guide plate-type paddle may be used to directionalize devices such as lasers, optical detectors (camera's, photodiodes, etc.), and/or other types of sensors. In other embodiments, the guide plate-type paddle may be used itself as a barrier, for example, as a shutter for a vent to directionalize air or water flow, or block light (i.e., provide shade relative to a light source).

Furthermore, it should be understood by those having ordinary skill that the present invention shall not be limited to specific examples depicted in the Figures and described in the specification. While the present invention has been described with respect to a limited number of embodiments, those skilled in the art, having benefit of this disclosure, will appreciate that other embodiments may be devised which do not depart from the scope of the invention as described herein. Accordingly, the scope of the invention should be limited only by the attached claims.

What is claimed is:

1. An actuator device, comprising:
a first actuating segment of a twist-spun artificial muscle fiber, wherein one end of the first actuating segment is at least connected to a first electrical terminal and the other end of the first actuating segment is at least connected to a second electrical terminal;
a second actuating segment of a twist-spun artificial muscle fiber, wherein one end of the second actuating segment is at least connected to a third electrical terminal and the other end of the second actuating segment is at least connected to a fourth electrical terminal;
a paddle disposed on both the first and second actuating segments; and
a heating provision connected to the first and second actuating segments, wherein the heating provision independently provides energy in the form of heat to the first and second actuating segments,
wherein the actuator device moves the paddle to a desired position through activating the first or second actuating segments; and an electrical stop that stops rotation of the paddle when the electrical stop electrically contacts the paddle.

2. The device of claim 1, further comprising:
wherein the first and second actuating segments are arranged linearly, and the second electrical terminal and the third electrical terminal are connected electrically.

3. The device of claim 2, further comprising: at least one guide bearing disposed on the paddle.

4. The device of claim 2, further comprising: a sensor apparatus that detects the angular position of the paddle.

5. The device of claim 1, wherein the paddle comprises a planar surface that is orientated parallel to an axis of rotation of the actuating device.

6. The device of claim 1, wherein the heating provision is a conducting material heated electrically.

7. The device of claim 1, wherein the heating provision is a conducting material heated electrically using pulse width modulation (PWM).

8. The device of claim 1, wherein each of the first and second actuating segments comprise a polymer fiber selected from the group consisting of nylon 6, nylon 6,6, polyethylene, polyvinylidene fluoride, and combinations thereof.

9. The device of claim 1, wherein each of the first and second actuating segments comprises carbon nanotubes (CNT).

10. The device of claim 5, wherein each of the first and second actuating segments further comprises paraffin wax.

11. The device of claim 1, wherein the paddle is a directional guide.

12. The device of claim 11, wherein an optical detector is mounted on the paddle.

13. The device of claim 1, further comprising:
each of the first electrical terminal, the second electrical terminal, the third electrical terminal and the fourth electrical terminal being spaced apart from the paddle.

14. The device of claim 1, wherein, by activating and deactivating at least one of the first actuating segment and the second actuating segment, the paddle is configured to be rotated in a first direction and a second direction that is opposite the first direction.

15. A method for manufacturing an actuator device, the method comprising:
twisting an artificial muscle fiber comprising nanofibers and an actuating yarn guest that is operable for undergoing change in volume by a change process;
setting the artificial muscle fiber by thermally annealing the nanofibers and the actuating yarn guest;
cutting the artificial muscle fiber into first and second actuating segments;
fixing one end of the first actuating segment to at least a first electrical terminal and the other end to at least a second electrical terminal;
fixing one end of the second actuating segment to at least a third electrical terminal and the other end to at least a fourth electrical terminal;
disposing a paddle on both the first and second actuating segments; and
disposing a heating provision to the first and second actuating segments, wherein the heating provision independently provides energy in the form of heat to the first and second actuating segments,
wherein the actuator device rotatably moves the paddle to a desired position through activating the first or second actuating segments using the heating provision, and an electrical stop that stops rotation of the paddle when the electrical stop electrically contacts the paddle.

16. The method according to claim 15, further comprising:
providing the first electrical terminal and the second electrical terminal adjacent to each other, and
providing the third electrical terminal and the fourth electrical terminal adjacent to each other.

17. The method according to claim 15, further comprising:
providing each of the first electrical terminal, the second electrical terminal, the third electrical terminal and the fourth electrical terminal so as to be spaced apart from the paddle.

18. The method of claim 15, further comprising:
activating and deactivating at least one of the first actuating segment and the second actuating segment such that the paddle rotates in a first direction and a second direction that is opposite the first direction.

19. An actuator device, comprising:
a first actuating segment of a twist-spun artificial muscle fiber, wherein one end of the first actuating segment is at least connected to a first electrical terminal and the other end of the first actuating segment is at least connected to a second electrical terminal;
a second actuating segment of a twist-spun artificial muscle fiber, wherein one end of the second actuating segment is at least connected to a third electrical terminal and the other end of the second actuating segment is at least connected to a fourth electrical terminal;
a paddle disposed on both the first and second actuating segments; and
a heating provision connected to the first and second actuating segments, wherein the heating provision independently provides energy in the form of heat to the first and second actuating segments, wherein the actuator device moves the paddle to a desired position through activating the first or second actuating segments, wherein the first electrical terminal and the second electrical terminal are adjacent to each other, and wherein the third electrical terminal and the fourth electrical terminal are adjacent to each other; and an electrical stop that stops rotation of the paddle when the electrical stop electrically contacts the paddle.

20. The device of claim 19, further comprising:
each of the first electrical terminal, the second electrical terminal, the third electrical terminal and the fourth electrical terminal being spaced apart from the paddle.

21. The device of claim 19, wherein, by activating and deactivating at least one of the first actuating segment and the second actuating segment, the paddle is configured to be rotated in a first direction and a second direction that is opposite the first direction.

* * * * *